United States Patent [19]

Johnson et al.

[11] 4,292,327

[45] Sep. 29, 1981

[54] METHOD FOR TREATMENT OF HUMAN EYE DISEASE

[76] Inventors: Lewis A. Johnson, 1050 Park Ave., New York, N.Y. 10028; Emil Wirostko, E. 208 Midland Ave., Paramus, N.J. 07652

[21] Appl. No.: 135,887

[22] Filed: Mar. 31, 1980

Related U.S. Application Data

[62] Division of Ser. No. 932,904, Aug. 11, 1978, Pat. No. 4,220,657, which is a division of Ser. No. 453,463, Jan. 23, 1974, abandoned.

[51] Int. Cl.$^3$ ............................................. A61K 31/13
[52] U.S. Cl. .................................................... 424/325
[58] Field of Search ........................................ 424/325

[56] References Cited

U.S. PATENT DOCUMENTS 3,150,046  9/1964  Sensi ............................ 260/239.3 P
3,342,810  9/1967  Maggi .......................... 260/239.3 P

OTHER PUBLICATIONS

Alexander–Jackson, Growth, vol. 18, 1954, pp. 37–51.
Robson, Recent Advances in Pharm, Little, Brown & Co. 1956, pp. 268–270, 286–290.
The Stethoscope, Nov. 1974, p. 3.
Clinicat Trends, vol. 13, No. 6, Jan. 1975, pp. 1,4 & 5.
Medical Tribune & Med New, vol. 15, No. 44, Wed. Nov. 27, 1974, pp. 1, 25.

*Primary Examiner*—Anna P. Fagelson
*Attorney, Agent, or Firm*—Pennie & Edmonds

[57] ABSTRACT

Sterile aqueous humor from patients afflicted with the disease endogenous uveitis contains a previously unreported pathogenic microorganism, *Micromyces intracellularis,* which also has been found in tissue specimens from other diseases. When inoculated into an animal model (e.g., a mouse), the microorganism produces both chronic eye and systemic disease in addition to accelerated mortality and occasional psychotic animal behavior, metabolic disturbances, and neuro-muscular disorders, depending on the mode of inoculation. The animal model therefore provides the basis for a screening process to evaluate chemotherapeutic agents in the treatment of human disease. Using this animal model, a significant decrease in mortality associated with the introduction of *Micromyces intracellularis* is achieved by the application to the animal model of the chemotherapeutic agents d-2,2'-(ethylenediimino)-di-1-butanol, 4,4'-sulfonyldianiline, and 3[[(4-methyl-1-piperazinyl)-imino]-methyl]-rifamycin SV. These agents are therefore effective in the treatment of diseases having as their etiological agent *Micromyces intracellularis,* and are particularly useful in the chemotherapy of endogenous uveitis, conjunctivitis and kerato-conjunctivitis.

20 Claims, 1 Drawing Figure

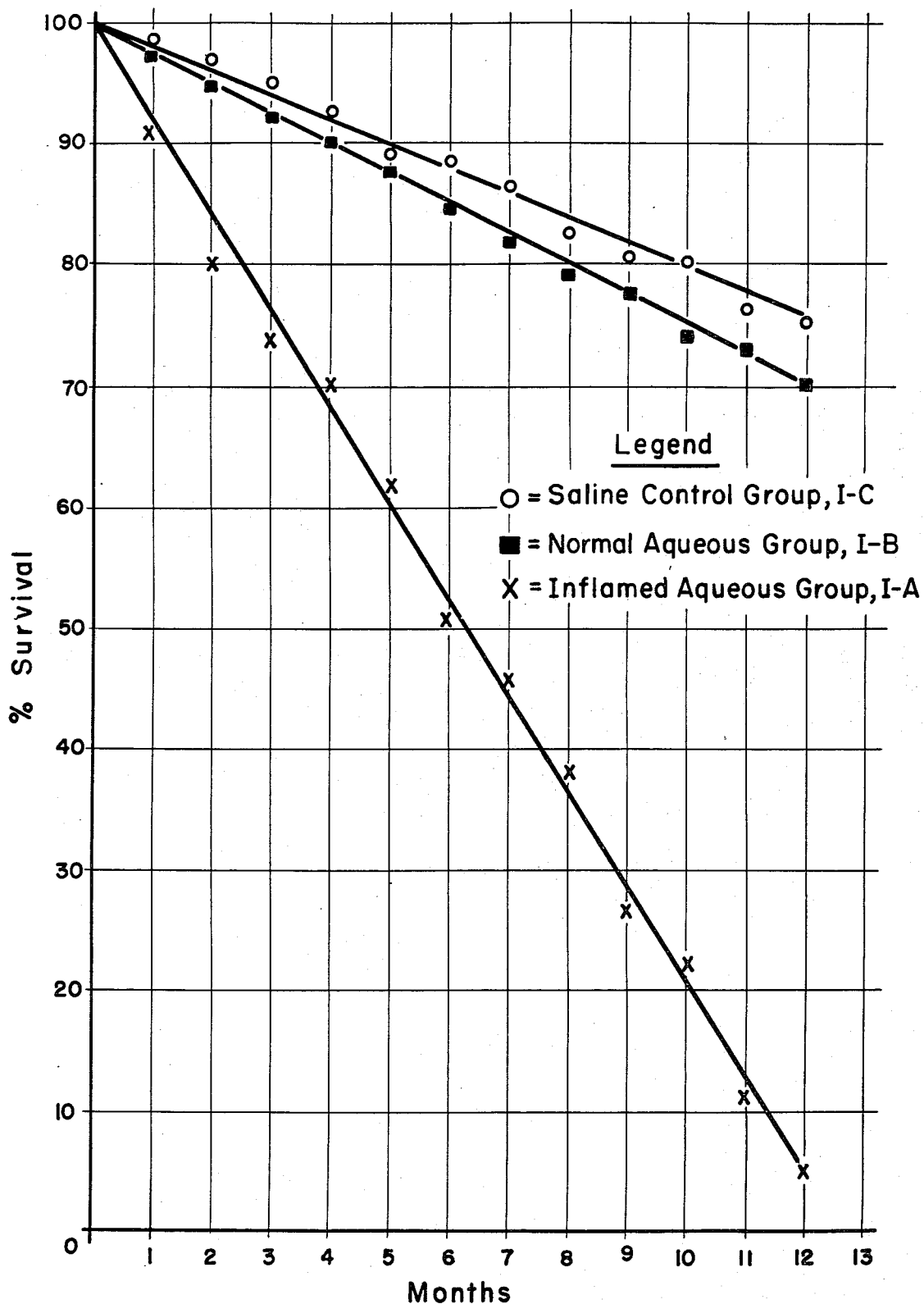

METHOD FOR TREATMENT OF HUMAN EYE DISEASE

This is a division of application Ser. No. 932,904, filed Aug. 11, 1978, now U.S. Pat. No. 4,220,657, which is a division of application Ser. No. 453,463, filed Jan. 23, 1974, now abandoned.

BACKGROUND OF THE INVENTION

This invention relates to the treatment of human disease. More particularly, it relates to the recovery and identification of a hitherto unknown infectious microorganism, the application of this pathogen to laboratory animals, and to novel indications for the use of certain known chemotherapeutic agents in the treatment of human diseases associated with the novel pathogen.

The search for new therapeutic agents and novel indications for existing drugs in the treatment of human diseases requires an animal model system related to each particular disease under investigation and which is responsive to a reproducible source of the infectious agent. Non-treated infected animals of the model must show symptoms or succumb to the disease in a regular, predictable manner. In addition, although some laboratory animals inoculated with a human disease-causing agent may show a syndrome with a long latent period, it must be possible to definitely associate the syndrome with the corresponding human chronic disease.

The isolation of a causative agent from human chronic inflammatory disease conditions capable of inducing those conditions in an animal model would therefore be an important breakthrough in the etiology of such human diseases.

Accordingly, it is an object of the present invention to provide a process for recovering an infectious microorganism from inflammatory disease tissue or fluid as the causative agent capable of inducing those disease conditions.

Another object of the present invention is to provide an animal model system responsive in a definite and predictable manner to a human disease-causing agent.

Another object is to provide novel indications for existing drugs and means for designing new therapeutic agents by means of an animal model.

These and other objects of the present invention as well as a fuller understanding of the advantages thereof can be had by reference to the following detailed description and claims.

DESCRIPTION OF THE INVENTION

The present invention is based on the discovery that sterile aqueous humor (eye fluid) from patients afflicted with endogeneous uveitis contains a unique and heretofore unreported pathogenic microorganism which can be observed with the light microscope. This pathogen has a complex life cycle, is not propagatable by the usual in vitro laboratory techniques, and when inoculated, say, subconjunctivally into one or both eyes of a host animal ("animal model"), produces both eye and systemic diseases, the latter being generally randomly distributed inflammatory diseases of any organ system and less commonly either degenerative or neoplastic in type. The accelerated mortality induced by the pathogen is accompanied occasionally by psychotic animal behavior, metabolic disturbances with glucosuria, and neuro-muscular disorders characterized by coarse head tremors, paresis, motor seizures and/or locomotor ataxia.

The new microorganism, which we have designated *Micromyces intracellularis*, has been recovered and identified from the inflammed aqueous humor of patients suffering from endogeneous uveitis. It differs from any of the known phyta listed in the accepted classification of Bergey's *Manual of Determinative Bacteriology* (7th edition, 1957). Individual microorganisms in this taxonomic system are distinguished, for purposes of classification, on the basis of morphological characteristics and biochemical behavior. Accordingly, it is believed that this novel organism constitutes a new family, Micromycetaceae, within the Order Actinomycetales because it has properties in common with other species of this order. A living culture of the organism has been deposited with the American Type Culture Collection at Rockville, Maryland and has been added to its permanent collection of microorganisms as ATCC 31,000.

The organism or agent cannot be propagated in vitro on bacteriological media, whether enriched or selective. A large variety of media have been tested, using varying atomspheric and temperature conditions, with no demonstrable growth after prolonged incubation, even up to twelve months. A large variety of tissue cultures also fail to propagate the organism.

The organism has a complex growth cycle, both intra- and extracellularly, during which a wide variety of morphologically distinctive parts are produced. These parts have quite variable tinctorial properties.

In a fresh aqueous suspension of *Micromyces intracellularis* small coccal particles can be observed which are approximately 1 to 2 microns in diameter, and have a distinctive, small amplitude, rapid, back-and-forth motility, which differs from Brownian movement. This motility is readily appreciated with both dark field and phase contrast microscopic techniques.

The use of tissue smears is the best way to demonstrate the complete life cycle of the agent. The organism parasitizes a wide variety of both fixed and wandering cells. This is best appreciated in epithelial and endothelial cells where a large number of varying sized, inclusion-like particles can be seen within the cytoplasm in the earliest intracellular growth phase of the organism. One parasitized cell may contain many such particles. The smallest of these particles are often Gram positive, generally acid or basis staining, and Periodic Acid Schiff positive. These particles continue to develop intracellularly. Some appear destined to become larger intracytoplasmic coccal forms, whereas others develop into very fine filaments, a fraction of a micron in diameter, and into mats of these filaments. These fine filaments grow in length without any visible internal structure and with variable staining properties. Extracellularly, a filament may extend beyond the parasitized cell boundary for great distances where it undergoes further development and differentiation with the production of bacterial-shaped forms. As the filaments develop extracellularly they may show distinctive internal structure with vacuolization and bands being seen. The extracellular filaments also give rise to bacilli. The smallest bacilli may resemble safety pins in appearance. The largest bacilli produced are long, thick, vacuolated tubes. These bacillary bodies and tubes are generally Gram negative and have an affinity for acidophilic stains. Some of the most delicate filaments may be partly Periodic Acid Schiff positive and weakly acid fast. Coccal particles arising from the extracellular filament are quite distinctive morphologically. These can arise from the filament, like a row of peas, at varying intervals. The smallest of these coccal bodies is less than one micron in diameter, and the largest may be the size, say, of a polymorphonuclear leukocyte nucleus. Many of these extracellularly developing cocci appear to enlarge and to divide into pairs and tetrads with biscuit shapes. These cocci are generally Gram negative and only rarely Gram positive. These extracellularly developing cocci stain variably with both acid and basic stains, and they may be Periodic Acid Schiff positive. Although the smallest cocci are homogeneous in their staining, the larger cocci have internal structure demonstrable with the usual stains. At the terminus of the delicate, undifferentiated, extracellular portion of some of the filaments a cluster of spherical, uniform sized, tiny particles, similar to those seen in the cytoplasm of the parasitized cell, are occasionally seen.

In fixed tissue sections the finer intra-cytoplasmic forms described above are difficult to demonstrate. The filaments are most easily recognized when a large extracellular cluster of these stain basic with the usual tissue stains, such as Hematoxylin, giving the appearance of a dense mat. The pleomorphic cocci described above are widely distributed in varying numbers against this compact filamentous background. The larger cocci, because of their varying large size and basophilic staining properties, are indistinguishable from nuclear debris. Large clusters of the smaller, uniform-staining cocci resemble atypical eosinophil or basophil granules. The larger bacilli and sausage-shaped filaments are often difficult to recognize because they fail to stain well. When they do stain well with the basophilic stains, they may resemble compressed connective tissue nuclei. The Periodic Acid Schiff stain or silver stain, such as Gomori's Mathenamine Silver Stain, has a varying affinity for different internal structures, particularly in the larger cocci and filamentous structures, producing a granular or reticulated appearance. The outline of the individual forms are difficult to appreciate as they arise from the site of the parasitized groups of cells.

A wide variety of clinical (sterile) specimens containing the agent *Micromyces intracellularis* retain their infectivity after passing through millipore filters (e.g., Seitz-type filters), which normally prevent the passage therethrough of bacterial-size particles. Examples of such specimens include aqueous emulsions of colon carcinomas, hypertensive kidneys, arteriosclerotic aortic atheromas, myocardial infarctions, inflamed synovia from rheumatoid arthritis joints, lens cataracts, and body fluids such as diabetic urine and spinal fluid from patients with demyelinating diseases and psychiatric disorders. Filtered clinical specimens also retain their infectivity following storage in a cell-free, aqueous state at ordinary refrigerator temperatures (e.g., at between 4° and 7° C.) for up to twelve months and perhaps longer. Infectivity of the organism can be destroyed by autoclaving (15 p.s.i.g./15 minutes/212° F.), by boiling for 10 minutes, or by treatment with phenol.

The pathogen described hereinabove has been found in acute and chronic endogeneous uveitis, acute and chronic non-specific keratoconjunctivitis, chronic keratitis, chronic conjunctivitis, chronic corneal ulcer, orbital cellulitis and may be found in non-specific inflammtory diseases of any human organ system.

Host organisms which can serve as the animal model of the present invention include, without limitation, fowl (e.g., chickens), primates (e.g., chimpanzees), rodents (e.g., mice, rats, rabbits, guinea pigs), cattle, horses, pigs, dogs, cats and the like.

Inoculation of *Micromyces intracellularis* into sites of the animal model other than the eye produces local inflammatory and, less frequently, degenerative or neoplastic lesions, in addition to the ocular and systemic diseases and accelerated mortality described earlier and in greater detail hereinbelow. By "inoculation," it is understood to mean the term as it is commonly used in the medical arts, including oral inoculation, parenteral inoculation (e.g., intravenous, intra-articular, subcutaneous, intra-peritoneal, intradermal, intramuscular and intrathecal inoculation) and topical inoculation (e.g., mucosal, conjunctival, and dermal application). The modes of inoculation described above are also applicable to the administration of chemotherapeutic agents in the treatment of diseases having as their etiological agent the newly-discovered microorganism described hereinabove.

In measuring the response of the animal model inoculated with *Micromyces intracellularis*, any of a number of recognized methods can be used, including mortality, general morbidity, visual inspection of morbidity at the site of inoculation, histology, and quantitation of the infectious agent present in the animal model tissue.

INOCULATION OF THE ANIMAL MODEL

The following procedures illustrate the techniques for inoculating mice with sterile materials containing *Micromyces intracellularis* as an animal model according to the present invention. It should be understood that the procedures described hereinbelow can be varied within the scope of the present invention and are generally applicable to any host organism suitable for use in the animal model of the present invention.

I. PATHOGENICITY OF ORGANISM INFECTED INFLAMED HUMAN AQUEOUS HUMOR

A. Sterile inflamed aqueous humor from 100 patients with acutely recurrent chronic endogenous uveitis was obtained by anterior chamber paracentesis. Each specimen was stored at 4° C. for 4 to 12 months, and individually inoculated, 0.05 cc per eye, subconjunctivally into each eye of 100 AKR 8 to 10 gram male mice.

B. Sterile aqueous humor from 100 eye bank eyes, observed to be grossly normal, was obtained by sterile paracentesis. In some cases, this material was composed of liquid-vitrous-aqueous mixture. Each specimen was stored at 4° C. for 4 to 12 months, and individually inoculated, 0.05 cc per eye, subconjunctivally into each eye of 100 AKR 8–10 gram male mice.

C. Sterile isotonic saline, 0.05 cc per eye, was subjunctivally inoculated into each eye of 100 AKR 8 to 10 gram male mice.

II. PATHOGENICITY OF ORGANISM INFECTED DIABETIC RETINOPATHY URINE

A. Sterile urine from 10 patients with Diabetic Retinopathy was stored at 4° C. for 4 to 12 months, and individually inoculated, 0.05 cc per eye, subconjunctivally into each eye of 100 AKR 8 to 10 gram male mice.

B. Sterile urine from 10 normal young volunteers was stored at 4° C. for 4 to 12 months, and individually inoculated, 0.05 cc per eye, subconjunctivally into each eye of 100 AKR 8 to 10 gram male mice.

C. Sterile isotonic saline, 0.05 cc per eye, was inoculated subconjunctivally into each eye of 100 AKR 8 to 10 gram male mice.

III. PATHOGENICITY OF ORGANISM INFECTED MULTIPLE SCLEROSIS CEREBRO-SPINAL FLUID

A. Sterile inflamed cerebro-spinal fluid from 10 institutionalized patients with active multiple sclerosis was stored at 4° C. for 4 to 12 months, and individually inoculated, 0.05 cc per eye, subconjunctivally into each of 100 AKR 8 to 10 gram male mice.

B. Sterile isotonic saline, 0.05 cc per eye, was subconjunctivally inoculated into each eye of 100 AKR 8-10 gram male mice.

IV. PATHOGENICITY OF ORGANISM INFECTED CATARACTOUS LENS HOMOGENATE

A. Mature cataracts from 10 patients, each emulsified in sterile distilled water (1:10) was stored at 4° C. for 4-12 months, tested for final bacterial sterility, and individually inoculated, 0.05 cc per eye, subconjunctivally into each eye of 100 PARIS 8-10 gram male mice.

B. Normal clear lenses from 10 eye bank eyes, each emulsified in sterile distilled water (1:10), was stored at 4° C. for 4-12 months, tested for final bacterial sterility, and individually inoculated, 0.05 cc per eye, subconjunctivally into each eye of 100 PARIS 8-10 gram male mice.

C. Sterile isotomic saline, 0.05 cc per eye, was subconjunctivally inoculated into each eye of 100 PARIS 8-10 gram male mice.

V. PATHOGENICITY OF ORGANISM INFECTED CHRONIC HUMAN CORNEAL STROMAL ULCERS

A. Inflamed corneal stroma was obtained by keratectomy from 10 patients with chronic sterile corneal stromal ulcers. Each specimen was emulsified in sterile distilled water (1:10), filtered (using a Millipore Corp. SXGS 025 0.22 μm filter), stored at 4° C. for 4-12 months, tested for final bacterial sterility, and individually inoculated, 0.05 cc per eye, subconjunctivally into each eye of 100 PARIS 8-10 gram male mice.

B. Sterile corneal stroma was obtained from 10 normal appearing cadaver corneas. Each specimen was emulsified in sterile distilled water (1:10), filtered as in V(A), above, stored at 4° C. for 4-12 months, tested for final bacterial sterility, and individually inoculated, 0.05 cc per eye, subconjunctivally into each eye of 100 PARIS 8 to 10 gram male mice.

C. Sterile isotonic saline, 0.05 cc per eye, was subconjunctivally inoculated into each eye of 100 PARIS 8 to 10 gram male mice.

VI. PATHOGENICITY OF ORGANISM INFECTED RHEUMATOID ARTHRITIS JOINTS

A. Synovial biopsy material was taken from ten patients with Active Rheumatoid Arthritis. Each inflamed specimen was emulsified in sterile distilled water (1:10), millipore filtered, stored at 4° C. for 4 to 12 months, tested for final bacterial sterility, and individually inoculated, 0.05 cc per eye, subconjunctivally into each eye of 100 AKR 8 to 10 gram male mice, 10 mice per specimen.

B. Synovial tissue was obtained from ten cadaver knee joints with no gross and histological evidence of joint disease. Each specimen was emulsified in sterile distilled water (1:10), filtered as above, stored at 4° C. for 4 to 12 months, tested for final bacterial sterility, and individually inoculated, 0.05 cc per eye, subconjunctivally into each eye of 100 AKR 8 to 10 gram male mice, 10 mice per specimen.

C. Sterile isotonic saline, 0.05 cc per eye, was subconjunctivally inoculated into each eye of 100 AKR 8 to 10 gram male mice.

VII. PATHOGENICITY OF ORGANISM INFECTED COLON CARCINOMAS

A. Colon carcinoma tissue was obtained from 10 patients with surgically resected specimens. Approximately 3 to 4 grams of the fungating and/or ulcerated portion of the tumor was emulsified in sterile distilled water (1:10), filtered as above, stored at 4° C. for 4 to 12 months, tested for final bacterial sterility, and individually inoculated, 0.05 cc per eye, subconjunctivally into each eye of 100 AKR 8-10 gram male mice, 10 mice per specimen.

B. Normal colonic mucosa was obtained from 10 grossly and histologically normal cadaver colons. Approximately 3-4 grams of the normal colon wall was emulsified in sterile distilled water (1:10), filtered as above, stored at 4° C. for 4-12 months, tested for final bacterial sterility, and individually inoculated, 0.05 cc per eye, subconjunctivally into each eye of 100 AKR 8-10 gram mice, 10 mice per specimen.

C. Sterile isotonic saline, 0.05 cc per eye, was subconjunctivally inoculated into each eye of 100 AKR 8-10 gram male mice.

VIII. PATHOGENICITY OF ORGANISM INFECTED STERILE POOLED GUINEA PIG PASSAGE EYE EMULSIONS

A. Guinea pig eyes from 100 guinea pigs, which died 3-6 months after subconjunctival inoculation with 0.1 cc of inflamed aqueous humor from 10 individual patients with Acute Exacerbations of Chronic Endogenous Uveitis, were pooled and emulsified (1:10) in sterile distilled water, filtered as above, stored at 4° C. for 4-12 months, tested for final bacterial sterility, and subconjunctivally inoculated, 0.05 cc per eye, into each eye of 100 AKR 8-10 gram male mice. (The presence of *Micromyces intracellularis* was verified in each of the 10 pairs of guinea pig eyes).

B. An autoclaved aliquot of the ten Group VIII-A emulsified guinea pig eyes was filtered as above, stored at 4° C. for 4-12 months, tested for final bacterial sterility, and subconjunctivally inoculated, 0.05 cc per eye, into each eye of 100 AKR 8-10 gram male mice.

C. A phenolized aliquot of the ten Group VIII-A emulsified guinea pig eyes (0.5 cc of phenol per 25 cc of aqueous emulsion incubated for 18 hours) was filtered as above, stored at 4° C. for 4-12 months, tested for final bacterial sterility, and subconjunctivally inoculated, 0.05 cc per eye, into each eye of 100 AKR 8-10 gram male mice.

D. An aliquot of the ten Group VIII-A emulsified guinea pig eyes was boiled for 10 minutes, filtered as above, stored at 4° C. for 4-12 months, tested for final bacterial sterility, and inoculated, 0.05 cc per eye, into each subconjunctiva of 100 AKR 8-10 gram male mice.

E. A pair of eyes from each of 10 guinea pigs, which were sacrificed 6 months after individual subconjunctival inoculation of 0.1 cc of aqueous humor from 10 grossly normal eye bank eyes, was individually emulsified (1:10) in sterile distilled water, filtered as above, stored at 4° C. for 4-12 months, tested for final bacterial sterility, and individually inoculated subconjunctivally, 0.05 cc per eye, into each eye of 10 AKR 8-10 gram male mice. (The presence of *Micromyces intracellularis* could not be detected in any of the ten specimens.)

F. Sterile isotonic saline, 0.05 cc per eye, was inoculated subconjunctivally into each eye of 100 AKR 8-10 gram male mice.

The observed pathogenicities resulting from the abovedescribed inoculations are summarized in Table I, below.

TABLE I

Pathogenicities Observed in the Mouse Animal Model

| GROUPS | PERCENT MORTALITY AT 12 MONTHS | STATISTICAL SIGNIFICANCE OF OBSERVED DIFFERENCES GROUPS | CHI-SQUARE* |
|---|---|---|---|
| I(A) | 95% | I(A) vs. I(B) | 92.9 |
| I(B) | 30% | I(A) vs. I(C) | 108 |
| I(C) | 25% | I(B) vs. I(C) | 0.9 |
| II(A) | 82% | II(A) vs. II(B) | 53.05 |
| II(B) | 32% | II(A) vs. II(C) | 67.6 |
| II(C) | 25% | II(B) vs. II(C) | 1.5 |
| III(A) | 65% | III(A) vs. III(B) | 33.95 |
| III(B) | 25% | — | — |
| IV(A) | 66% | IV(A) vs. IV(B) | 14.6 |
| IV(B) | 40% | IV(A) vs. IV(C) | 21.73 |
| IV(C) | 34% | IV(B) vs. IV(C) | 0.53 |
| V(A) | 78% | V(A) vs. V(B) | 39.2 |
| V(B) | 33% | V(A) vs. V(C) | 52.1 |
| V(C) | 26% | V(B) vs. V(C) | 0.865 |
| VI(A) | 62% | VI(A) vs. VI(B) | 23.3 |
| VI(B) | 29% | VI(A) vs. VI(C) | 29.38 |
| VI(C) | 25% | VI(B) vs. VI(C) | 3.06 |
| VII(A) | 64% | VII(A) vs. VII(B) | 24.66 |
| VII(B) | 28% | VII(A) vs. VII(C) | 32.39 |
| VII(C) | 25% | VII(B) vs. VII(C) | 0.41 |
| VIII(A) | 96% | VIII(A) vs. VIII(B) | 93.85 |
| VIII(B) | 22% | VIII(A) vs. VIII(F) | 113.6 |
| VII(C) | 25% | VIII(B,C,D) vs. VIII(F) | 0.111 |
| VIII(D) | 24% | — | — |
| VIII(E) | 31% | VII(E) vs. VIII(F) | 2.05 |
| VIII(F) | 23% | — | — |

*CHI-SQUARE$(\chi^2) = \Sigma \left[ \dfrac{(f_o - f)^2}{f} \right]$ where
$f_o$ = observed mortality rate
$f$ = expected (control mortality rate

APPEARANCE OF THE ANIMAL MODEL AFTER INOCULATION WTH CLINICAL HUMAN MATERIALS CONTAINING *MICROMYCES INTRACELLULARIS*

I. DIRECT EYE INOCULATION

A. Mice

During the first two weeks following inoculation of pretreated clinical materials containing *Micromyces intracellularis* subconjunctivally into 8-10 gram mice, no change is noted in the inoculated eyes or in the animal. During the 3rd or 4th week an occasional mouse (about 10%) demonstrates one or both eye lids closed by exudate for varying periods of time, usually several days, and about 5% demonstrate abnormal systemic changes such as decreased motor activity, dull coats, or bizarre motor activity. Increased mortality relative to control mice begins to be seen during the 3rd or 4th week following inoculation. By the end of the fourth week usually about 10% of the inoculated mice have died. During the next four weeks more eyes become closed, either one or both, for varying periods of time (usually several days but some eyes become permanently closed, so that by the end of the 8th week usually about 30-50% of the inoculated mice are affected. At this time usually about 20% of the inoculated mice will have died. This increased mortality rate among inoculated mice versus the mortality rate among control mice continues at a constant rate over the succeeding 44 weeks so that by the end of 12 months usually 65-95% of the inoculated mice (the exact percentage presumably depending on the initial concentration of the inoculum and variations in the host response) have died. Following inoculation, an occasional mouse will develop among other things, a pthisis bulbi, proptosis, a hematocele, or intra- and peri- ocular neoplasms. About 5% of the mice develop red, swollen joints and about an equal number demonstrate glucosuria, gait or locomotor abnormalities, motor seizures, or course head tremors either transiently or permanently. A graphical representation of the observed increase in mortality rate among the mice which were inoculated with *Micromyces intracellularis* according to procedures I(A)-(B), above, is presented in the accompanying drawing. It can be seen from the "survival curves" in the drawing that, by using an appropriate number of animals in the model system of the present invention (i.e., controls and experimentals), the required period of observation can, if desired, be appreciably shortened.

B. Guinea Pigs

During the first month following subconjunctival inoculation of sterile clinical materials containing *Micromyces intracellularis* into 150 gram guinea pigs, no ocular or systemic lesions are noted, but during the second month about 5% of the guinea pigs develop ocular suppuration characterized by hyperemic conjunctiva, sticky eye lids in the morning, and purulent discharge. Occasionally this rapidly progresses to a Phthisis bulbi. During the second month mortality begins to be seen. By the end of the third month about 10% of the guinea pigs develop eye suppuration and systemic lesions begin to be seen, such as weight loss, generalized lymphadenopathy, and hot, tender swollen joints. Mortality begins to increase during this time, and by the end of the fourth month another 10% of the inoculated animals show these systemic signs of disease. About 5% of the inoculated guinea pigs by the end of the fourth month demonstrate paresis of one or more extremities, a hemiparesis occasionally being seen. An equal number at this time demonstrate coarse, rhythmic head tremors, and about 5% during the third to fourth month will demonstrate glucosuria and occasionally hematuria and/or proteinuria. Usually by the sixth month the mortality among inoculated guinea pigs is 75–100%. (Symptoms of Conjunctivitis, Arthritis, Lymphadenitis, and wasting were not seen in control guinea pigs, where the mortality rate varied from 0–50% at six months).

II. Subcutaneous Inoculation at Sites Distant from the Eye

A. Mice

Subcutaneous inoculation of sterile clinical materials containing *Micromyces intracellularis* into the facial skin region results in puffy, red, swollen facial tissues in about 25% of the mice 2 to 4 weeks following inoculation. Facial alopecia at the inoculation site is occasionally seen during this time period. These lesions usually disappear by the sixth week but an occasional eye is seen to be closed for short periods of time prior to this. Mortality during the ensuing time period is similar to that described in the subconjunctival inoculation route.

When sterile clinical materials containing *Micromyces intracellularis* are inoculated subcutaneously in the skin of the sacral region, there result multiple erythematous plaques, macules, papules, pustules, and/or ulcers of the tails in about 25% of the mice 2–4 weeks after inoculation. Healing of these lesions is slow with occasional nodular, deformed tails being seen several weeks later. Other affected tails become gangrenous and slowly fall off, either at the tip or at other points between the tip and the base of the tail. About 25% of the mice develop, either with or without the above described tail disease, varying sized areas of alopecia, erythema, yellow greasy coats and/or ulcers at the site of inoculation. These frequently heal slowly during the ensuing weeks, but in many of the affected mice these lesions recur. Some of the affected mice became so debilitated in appearance, that death appears imminent during the 3rd and 4th month. However, some of these severely debilitated mice do survive as runts after 12 months of observation. About 10% of the mice so inoculated demonstrate one or both eyelids closed for several days at a time sometime during the course of observation. About 5% of the inoculated mice demonstrate red swollen joints for varying and protracted periods at various times during the course of observation, and about a similar percentage demonstrate bizarre motor activity, paresis, head tremors, or seizures, at one time or another during the course of observation. The 12-month mortality in the mice so inoculated is similar to that described for the subconjunctivally inoculated mice.

B. Guinea Pigs

The subcutaneous inoculation of sterile clinical materials containing *Micromyces intracellularis* does not result in observable cutaneous lesions during six months of observation. Lymphadenopathy and increased mortality such as described for the subconjunctival inoculation route is seen, however.

III. Intraperitoneal Inoculation

A. Mice

During the first week following intraperitoneal inoculation of sterile human disease materials containing *Micromyces intracellularis* into young mice systemic illness of varying degrees in the individual mice is produced. This illness is characterized by subdued spontaneous activity, rough coats, and huddling. Although an occasional mouse dies during the first week following intraperitoneal inoculation of the inoculum, most mice so inoculated recover from this initial phase of post-inoculation morbidity. Two weeks after inoculation, however, increased spontaneous mortality begins to occur in the inoculated mice as compared to control mice. This increased rate of mortality continues through succeeding weeks of observation at a rate comparable to other routes of inoculation, i.e., subconjunctival or subcutaneous inoculation. During the ensuing weeks of observation about 5 to 10% of the inoculated mice demonstrate varying degrees of coat changes—alopecia, greasy coats, dull or rough coats, macules or papules—and also demonstrate swollen joints, locomotor disturbances, seizures, jerky head tremors, or closed eye lids. Sometimes these abnormalities are present for only a few days, but they are usually followed by death of the mouse within a few days after their occurrence.

B. Guinea Pigs

During the initial 10 to 12 weeks, following intraperitoneal inoculation of sterile human disease materials containing *Micromyces intracellularis* into young guinea pigs produces no observable change in the appearance of the animal. Thereafter, about 25% of the inoculated guinea pigs begin to demonstrate evidence of systemic illness usually manifested by varying combinations of the following signs: rapid weight loss, paresis, swollen joints, jerky head movements, and/or marked soft peripheral lymphadenopathy. Accelerated mortality, as compared to controls, begins to occur and usually about 85–100% of the inoculated guinea pigs are dead by the end of the sixth month following inoculation.

The data contained in the following Table II are based on observation using 200 CF (Carworth Farms) outbred mice, 100 experimental and 100 control, for each mode of inoculation. These data provide a general classification of the pathologic lesions observed and their incidence when the mouse is used for the modelling of chronic human disease due to *Micromyces intracellularis*.

TABLE II

| Mode of Inoculation | General Classification of Pathologic Lesions | Incidence Experimental | Control | Chi Square |
| --- | --- | --- | --- | --- |
| Subconjunctival | Chronic Inflammatory Eye Disease | 100% | 0% | 196.0 |
| | Degenerative Eye Disease | 75% | 0% | 116.8 |
| Subcutaneous | Chronic Inflammatory Skin Disease | 25% | 0% | 26.33 |
| | Degenerative Skin Disease | 25% | 0% | 26.33 |
| Intraperitoneal | Chronic Inflammatory Systemic Disease | 75% | 2% | 109.5 |
| | Degenerative Systemic Disease | 25% | 2% | 20.72 |

The date contained in Table III, below, are based on special microscopic pathologic observations in 1000 mice and 100 guinea pigs inoculated into a variety of sites (e.g., interperitoneal, subcutaneous back and subconjuctival) with sterile clinical materials containing *Micromyces intracellularis*. Local inoculation of the agent into each of the organs listed in Table III can be expected to produce a greater incidence of the described lesion at the inoculation site.

chemotherapeutics, for the diagnosis and treatment of disease.

Using the animal model described above, it has been discovered according to the present invention that certain chemotherapeutic agents are effective in protecting the animal model from the significantly increased mortality associated with the introduction therein of the

TABLE III

| | | % INCIDENCE | | | |
|---|---|---|---|---|---|
| | | EXPERIMENTAL | | CONTROL | |
| ORGAN | DESCRIPTION OF LESION | MICE | GUINEA PIG | MICE | GUINEA PIG |
| HEART | Subendocardial Aschoff Nodules in both mice & guinea pigs, Subendocardial fibrinoid necrosis in mice, sarcomyolysis of myocardium in guinea pigs. | 10% | 25% | 2% | 0% |
| SPLEEN | Splenomegaly; acute or subacute splenitis, atypical lymphoid hyperplasis in both mice and guinea pigs. | 50% | 50% | 5% | 0% |
| SKIN | (SUBCUTANEOUS INCOCULATION) Chronic panniculitis, granulomas, acute and chronic ulcers, fibrosis, dermal adnexal atrophy, necrosis | 20% | 5% | 0% | 0% |
| LYMPH NODES | Marked reactive lymphoid hyperplasia in mice and guinea pigs, atypical lymphoid hyperplasia in mice, granulomatous lymphadenitis in guinea pigs, necrotic nodes in guinea pigs. | 20% | 10% | 2% | 0% |
| JOINTS | Rheumatoid nodules around joint cavity in mice & guinea pigs, papillary synovitis in mice, extensive periarticular fibromatosis in guinea pigs, calcified focal necrosis in tendons of guinea pigs, acute and chronic synovitis in mice and guinea pigs. | 10% | 20% | 0% | 0% |
| CENTRAL AND PERIPHERAL NERVOUS SYSTEM | Focal acute inflammation in peripheral nerves, cerebral cortex, spinal cord or meninges | 5% | 5% | 0% | 0% |
| EYES | (INTERPERITONEAL INOCULATION) | 20% | 20% | 0% | 0% |
| | (SUBCONJUNCTIVAL INOCULATION) Acute and chronic uveal tract inflammation, optic nerve meningitis, episcleritis, cataracts, anterior and posterior synecchia, interstitial keratitis, retinopathy, optic neuritis, orbital pseudotumers, extraocular muscle myositis | 100% | 50% | 0% | 0% |

Based on the above-described details of the animal model and unique microbial agent found in association with the foregoing lesions, the animal model is useful in the present invention for the development of diagnostic materials, such as antigens for in vivo and in vitro diagnostic tests, and therapeutic agents such as vaccines and pre-tested inoculum. In particular, it has been found that d-2,2'-(ethylenediimino)-di-1-butanol (also known as "ethambutol") which has the formula:

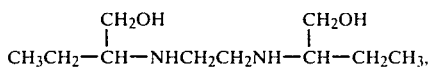

4,4'-sulfonyldianiline (also known as "dapsone") which has the formula:

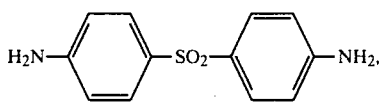

and 3-[[(4-methyl-1-piperazinyl)imino]methyl]-rifamycin SV (also known as "rifampin") which has the following formula:

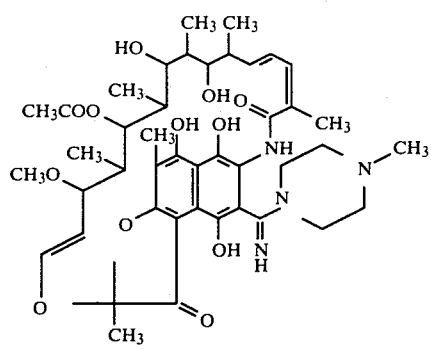

are useful chemotherapeutics in the practice of the present invention, particularly in the treatment of diseases associated with the above-described *Micromyces intracellularis*. These compounds are known compositions of matter and procedures for obtaining them will be apparent to those skilled in the synthetic organic or pharmaceutical arts.

Thus, ethambutol can be synthesized by heating ethylene dichloride with (+)-2-aminobutanol or, alternatively, by alkylating 2-aminobutanol with glyoxal using NaBH$_4$ as a reducing agent according to Wilkinson et al., *J. Am. Chem. Soc.*, 83, 2212 (1961). Pharmaceutical grade ethambutol (hydrochloride) is commercially available from American Cyanamid Co. under the trade name "Myambutol." Likewise, dapsone can be made starting from para-chloronitrobenzene according to the method described in U.S. Pat. No. 2,385,899 (1945) and is commercially available in a form suitable for chemotherapeutic use from Imperial Chemicals Ltd. under the trade name "Avlosulfon." Finally, rifampin is described in Allen et al., *Drug Intel. Clin. Pharm.*, 5(11), 364 (1971) and is available in a form suitable for medicinal use from Giba-Geigy Corp. under the trade name "Rimactane."

DESCRIPTION OF PREFERRED EMBODIMENTS

The following examples are provided for the purpose of further illustrating, without limitation, the animal model of the present invention and the application of the above-mentioned therapeutic agents to the treatment of diseases associated with the novel pathogen.

EXAMPLE I

Two hundred male AKR strain mice, ranging in age from 8 to 10 weeks, were obtained from the Jackson Laboratories, Bar Harbor, Maine and held for stabilization for a period of two weeks. At the end of this time, the mice were divided equally into five groups, A, B, C, D and E of forty mice each as follows:

Each animal in Groups A, B, C and D was subconjunctivally inoculated in each eye with a 0.05 milliliter aliquot of pooled, sterile aqueous humor specimens from patients with active endogenous uveitis and containing *Micromyces intracellularis*.

Group A mice each thereafter received daily oral dosing with 0.1 milliliter of an aqueous suspension containing 25 milligrams of ethambutol per kilogram of body weight for the first two months of the experiment. For the remaining ten months of the experiment, the concentration of ethambutol per daily dosage was reduced to 15 milligrams per kilogram of body weight.

Group B mice each thereafter received daily oral dosing with 0.1 milliliter of an aqueous suspension of 10 milligrams of rifampin per kilogram of body weight, for the duration of the experiment.

Group C mice each thereafter received daily oral dosing with 0.1 milliliter of an aqueous solution of 1 milligram of dapsone per kilogram of body weight, for the duration of the experiment.

Group D mice each thereafter received daily oral dosing with 0.1 milliliter of sterile, distilled water for the duration of the experiment.

Each animal in Group E (the "negative control group") was subconjunctivally inoculated with 0.05 milliliter of sterile isotonic saline solution. Each mouse in this group thereafter received oral dosing with 0.1 milliliter of sterile, distilled water for the duration of the experiment.

The five groups of animals were observed for 12 months to detect spontaneous mortality. The results at the end of this time were as follows:

| Group | Absolute Mortality | % Mortality |
|---|---|---|
| Group A | 24 | 60 |
| Group B | 26 | 65 |
| Group C | 28 | 70 |
| Group D | 34 | 85 |
| Group E | 20 | 50 |

The statistical significance of the mortality rates observed in this example is as follows:

Group A versus Group D $x^2 = 5.07$
Group B versus Group D $x^2 = 3.266$
Group C versus Group D $x^2 = 1.8$
Group D versus Group E $x^2 = 9.63$ Based on these statistical calculations, it can be concluded that the pathogen-inoculated animal model of the present invention exhibits a highly significant mortality rate compared to saline-inoculated negative control animals. Also, it can be seen that ethambutol, rifampin and dapsone all convey significant protection against the mortality seen in the animal model.

EXAMPLE II

As an example of the utility of the foregoing three chemotherapeutic agents based on the animal model, it has been found that ethambutol is especially effective in treating endogenous uveitis. In a noncontrolled study over a period of five years, a large number of patients, more than 50, were treated with systemic ethambutol. Some patients remained symptom free while taking the medicine; when the treatment was discontinued the disease returned in its full severity. Upon restarting the drug the eye inflammation again resolves in several weeks. This cycle was repeatedly observed in many patients over prolonged periods of time. Other patients have had their long-standing disease cured with prolonged drug treatment.

In a controlled experiment using ethambutol for a double-blind cross-over study, 41 patients were treated and followed for one-year's time. It was found from a follow-up treatment of 20 patients that the drug is more effective than placebo in suppressing the disease. Many of the patients in this controlled study have had disease of many years duration terminated with a few months of therapy.

In addition to the treatment of endogenous uveitis, other diseases can be treated with the aforementioned chemotherapeutics. Thus, an isotonic aqueous solution of ethambutol instilled daily in the conjunctival sac has been found to be efficacious in relieving signs and symptoms of chronic conjunctivitis, kerato-conjunctivitis and keratitis. The drug has also been given orally and topically for these conditions and appears to be similarly effective.

The present invention has been described with reference to certain specific embodiments which have been presented for purposes of illustration. It is to be understood, however, that numerous variations of the invention can be made which are well within the scope and spirit of the invention as described in the following claims.

We claim:

1. A method of treating active endogenous uveitis caused by *Micromyces intracellularis* comprising administering to a patient having endogenous uveitis an effective amount therefor of a therapeutic agent comprising d-2,2'-(ethylenediimino) di-1-butanol.

2. A method of treating endogenous uveitis according to claim 1 wherein the therapeutic agent is administered subconjunctvally into the affected eye.

3. A method of treating endogenous uveitis according to claim 1 wherein the therapeutic agent is administered in the form of an aqueous isotonic solution.

4. A method of treating endogenous uveitis according to claim 1 wherein the therapeutic agent is administered orally.

5. A method of treating endogenous uveitis according to claim 1 wherein the therapeutic agent is administered topically to the affected eye.

6. A method of treating chronic conjunctivitis caused by *Micromyces intracellularis* comprising administering to a patient having chronic conjunctivitis an effective amount therefor of a therapeutic agent comprising d-2,2'-(ethylenediimino)di-1-butanol.

7. A method of treating chronic conjunctivitis according to claim 6 wherein the therapeutic agent is administered subconjuctivally into the affected eye.

8. A method of treating chronic conjunctivitis according to claim 6 wherein the therapeutic agent is administered in the form of an aqueous isotonic solution.

9. A method of treating chronic conjunctivitis according to claim 6 wherein the therapeutic agent is administered orally.

10. A method of treating chronic conjunctivitis according to claim 6 wherein the therapeutic agent is administered topically to the affected eye.

11. A method of treating kerato-conjunctivitis caused by *Micromyces intracellularis* comprising administering to a patient having kerato-conjunctivitis an effective amount therefor of a therapeutic agent comprising d-2,2'-(ethylenediimino1(di-1-butanol.

12. A method of treating kerato-conjunctivitis according to claim 11 wherein the therapeutic agent is administered subconjunctivally into the affected eye.

13. A method of treating kerato-conjunctivitis according to claim 11 wherein the therapeutic agent is administered in the form of an aqueous isotonic solution.

14. A method of treating kerato-conjunctivitis according to claim 11 wherein the therapeutic agent is administered orally.

15. A method of treating kerato-conjunctivitis according to claim 11 wherein the therapeutic agent is administered topically to the affected eye.

16. A method of treating keratitis caused by *Micromyces intracellularis* comprising administering to a patient having keratitis an effective amount therefor of a therapeutic agent comprising d-2,2'-(ethylenediimino)di-1-butanol.

17. A method of treating keratitis according to claim 16 wherein the therapeutic agent is administered subconjunctivally into the affected eye.

18. A method of treating keratitis according to claim 16 wherein the therapeutic agent is administered in the form of an aqueous isotonic solution.

19. A method of treating keratitis according to claim 16 wherein the therapeutic agent is administered orally.

20. A method of treating keratitis according to claim 16 wherein the therapeutic agent is administered topically to the affected eye.

* * * * *